(12) United States Patent
Belcheva et al.

(10) Patent No.: US 8,888,828 B2
(45) Date of Patent: Nov. 18, 2014

(54) COMPOSITE FIXATION DEVICE

(75) Inventors: Nadya Belcheva, Hamden, CT (US);
Joseph Hotter, Middletown, CT (US);
Russell Heinrich, Madison, CT (US)

(73) Assignee: Covidien LP, Mansfield, MA (US)

( * ) Notice: Subject to any disclaimer, the term of this patent is extended or adjusted under 35 U.S.C. 154(b) by 588 days.

(21) Appl. No.: 12/780,110

(22) Filed: May 14, 2010

(65) Prior Publication Data
US 2011/0015684 A1 Jan. 20, 2011

Related U.S. Application Data

(60) Provisional application No. 61/226,022, filed on Jul. 16, 2009.

(51) Int. Cl.
| A61B 17/58 | (2006.01) |
| A61B 17/84 | (2006.01) |
| A61L 31/12 | (2006.01) |
| A61F 2/08 | (2006.01) |
| A61L 31/14 | (2006.01) |
| A61B 17/86 | (2006.01) |

(52) U.S. Cl.
CPC ............ *A61B 17/864* (2013.01); *A61L 31/128* (2013.01); *A61F 2/0811* (2013.01); *A61F 2210/0004* (2013.01); *A61L 31/129* (2013.01); *A61B 17/8625* (2013.01); *A61F 2002/0858* (2013.01); *A61F 2250/003* (2013.01); *A61B 17/866* (2013.01); *A61L 31/148* (2013.01); *A61L 31/127* (2013.01)

USPC ............ 606/331; 606/300; 606/301; 606/314

(58) Field of Classification Search
USPC .......... 606/300, 301, 309, 321, 328, 331, 314
See application file for complete search history.

(56) References Cited

U.S. PATENT DOCUMENTS

| 3,636,956 | A | | 1/1972 | Schneider |
| 4,599,085 | A | | 7/1986 | Riess et al. |
| 4,743,257 | A | | 5/1988 | Tormala et al. |
| 4,844,854 | A | | 7/1989 | Kaplan et al. |
| 4,916,193 | A | | 4/1990 | Tang et al. |
| 5,084,051 | A | | 1/1992 | Tormala et al. |
| 5,317,064 | A | | 5/1994 | Spinu |
| 5,348,026 | A | | 9/1994 | Davidson |
| 5,415,655 | A | * | 5/1995 | Fuller et al. ................. 606/16 |
| 5,869,170 | A | * | 2/1999 | Cima et al. ............... 428/304.4 |
| 6,589,245 | B1 | | 7/2003 | Weiler et al. |
| 6,863,671 | B1 | | 3/2005 | Strobel et al. |
| 7,179,883 | B2 | | 2/2007 | Williams et al. |
| 7,235,079 | B2 | | 6/2007 | Jensen et al. |
| 7,261,716 | B2 | * | 8/2007 | Strobel et al. .............. 606/314 |
| 7,268,205 | B2 | | 9/2007 | Williams et al. |
| 2004/0078090 | A1 | | 4/2004 | Binette et al. |

(Continued)

FOREIGN PATENT DOCUMENTS

| EP | 2005975 A2 | 12/2008 |
| WO | 82/00755 | 3/1982 |

*Primary Examiner* — Christian Sevilla

(57) ABSTRACT

A composite fixation device is described herein which includes a first and second biodegradable material. The first and second biodegradable materials degrade at different rates thereby permitting tissue ingrowth into the device prior to degradation of the entire device.

14 Claims, 5 Drawing Sheets

(56) References Cited

U.S. PATENT DOCUMENTS

| | | |
|---|---|---|
| 2004/0247644 A1 | 12/2004 | Bratt et al. |
| 2005/0008620 A1* | 1/2005 | Shimp et al. ............... 424/93.7 |
| 2005/0136764 A1 | 6/2005 | Sherman |
| 2006/0149266 A1 | 7/2006 | Cordasco |
| 2006/0276788 A1 | 12/2006 | Berry et al. |
| 2007/0156145 A1 | 7/2007 | Demakas et al. |
| 2009/0254051 A1* | 10/2009 | Von Oepen et al. .......... 604/272 |
| 2010/0042167 A1* | 2/2010 | Nebosky et al. .............. 606/315 |

\* cited by examiner

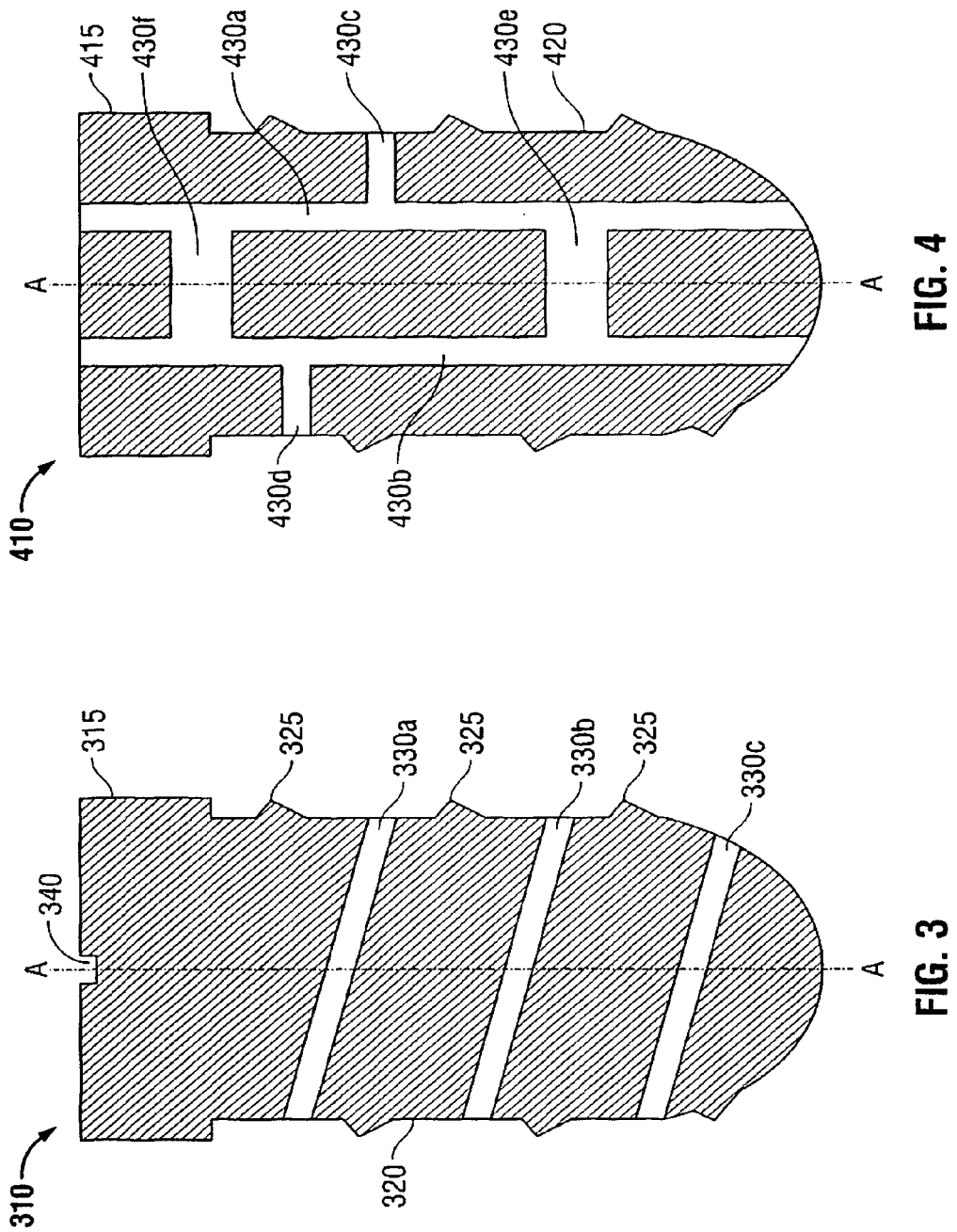

COMPOSITE FIXATION DEVICE

CROSS-REFERENCE TO RELATED APPLICATION

The present application claims the benefit of and priority to U.S. Provisional Application Ser. No. 61/226,022, filed on Jul. 16, 2009, the entire disclosure of which is incorporated herein by reference.

BACKGROUND

1. Technical Field

The present disclosure relates to a composite fixation device, and more particularly to a composite fixation device having a body made from a first biodegradable material. The device also includes at least one channel defined therein which includes a second biodegradable material, wherein the second biodegradable material degrades faster than the first biodegradable material.

2. Background of Related Art

Fixation devices may be threaded or non-threaded and are used to draw together and/or hold fragments of fractured bones, as well as soft tissues, to hard tissues. These devices may be used alone, for example, to attach a ligament to a bone, and/or in combination with other fixation devices, for example, to secure a bone plate to a fractured bone on opposing sides of a fracture. To place a fixation device in bone or tissue, the device is driven (e.g., turned or forced by contact) into a hole in the bone or tissue, such that the body of the device or a thread on the body of the device engages the bone or tissue around the hole. The device may be threaded along some or all of its length.

Fixation devices are known to be made of biodegradable materials or non-biodegradable materials. Devices made from biodegradable materials can be substantially broken down by the body but may provide less structural support than devices made from non-biodegradable materials. A biodegradable device allows the surrounding bone and/or tissue, with time, to integrate into the device. Biodegradable fixation devices may be more difficult to drive into bone or hard tissue without damaging the device. Moreover, because the devices are soft, the devices are often hollow along their length to provide additional surface area for engaging a driver and/or permitting tissue to enter the device following implantation.

Improved fixation devices, including biodegradable components, remain desirable.

SUMMARY

The present disclosure provides composite fixation devices which offer increased structural integrity because they do not immediately contain any openings therein, but allow for tissue integration over time as portions of the device degrade in vivo. In some embodiments, a device of the present disclosure may include a body made from a first biodegradable material and at least one channel. The channel(s) includes a second biodegradable material which degrades faster than the first biodegradable material. In some embodiments, the channel may be centrally located and extend along the entire length of the device. In embodiments, at least a portion of the channel is positioned along an exterior portion of the device.

In addition, composite interference screws are disclosed which include: a body made from a first biodegradable material, the body including a head; at least one thread extending axially around the outer perimeter of the body; and at least one channel defined within a portion of the device. The channel(s) include a second biodegradable material, wherein the second biodegradable material degrades faster than the first biodegradable material. In certain embodiments, the channel(s) may extend through a portion of the thread positioned axially around the outer perimeter of the body of the device.

BRIEF DESCRIPTION OF THE DRAWINGS

Various embodiments of the present disclosure will be discussed in more detail below in conjunction with selected embodiments and the appended drawings wherein:

FIG. 3 shows a cross-sectional view of the composite fixation device of FIG. 2;

FIG. 4 shows a cross-sectional view of another embodiment of a composite fixation device according to the present disclosure;

DETAILED DESCRIPTION

Figure 1:
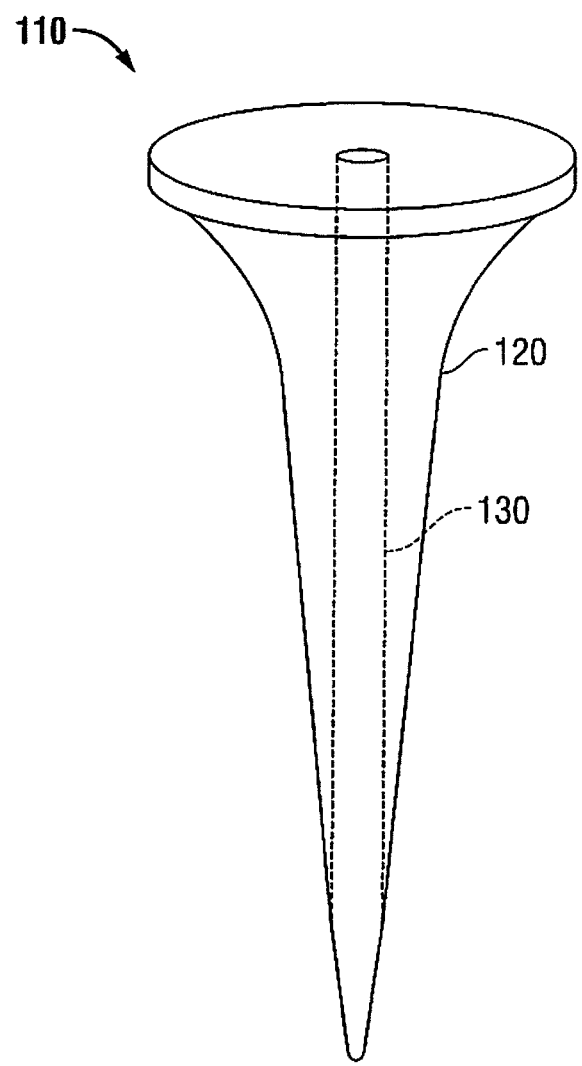
FIG. 1 shows a perspective side view of one embodiment of a composite fixation device according to the present disclosure.

The present disclosure describes a composite fixation device which includes a body made from a first biodegradable material and at least one channel defined within a portion of the body. The channel includes a second biodegradable material, wherein the second biodegradable material degrades at a faster rate than the first biodegradable material.

The composite fixation devices described herein are biocompatible and include at least two different biodegradable materials that upon implantation, degrade at different rates of time upon implantation. The combination of the two different biodegradable materials provides fixation devices with enhanced structural integrity in addition to the ability to promote tissue integration over time. In addition, degradation of the second biodegradable material, as noted above, degrades at a rate faster than the first biodegradable material, providing the composite devices with the ability to form and/or create openings in the device for tissue integration after being driven into the bone and/or tissue. The formed openings will allow the bone and/or tissue surrounding the site of implantation to grow into the device and become integrated with the portions of the composite device that are made from the slower degrading biodegradable material, i.e., the first biodegradable material. The integration of tissue into portions of the device further anchors the device at the site of implantation and allows the natural tissue to slowly replace the biodegradable device. A few non-limiting examples of suitable fixation devices include orthopedic devices such as surgical pins, bone and interference screws, suture anchors, nails, and the like.

A biodegradable material, as used herein, is any material that is substantially broken down (i.e., resorbed, degraded, dissolved, cleaved, and/or disintegrated, among others) over time in the body. Breakdown of the biodegradable materials may include and/or be followed by removal, restructuring, assimilation, and/or excretion, among others, of the broken down material. In embodiments, the biodegradable materials may be any material that is at least substantially replaced by tissue or bone during and/or after biodegradation. Replacement by tissue or bone may include macroscopically, microscopically, and/or atomically restructuring the biodegradable material in situ and/or removing it. The biodegradable materials may be configured to be biodegraded substantially over any suitable period of time, such as from about one day, one week, one month, three months, six months, one year, two years, five years, etc.

The first biodegradable material degrades or loses strength at a slower rate of time than the second biodegradable material. The first biodegradable material may be configured to degrade over a relatively longer period of time, for example, more than about three months (such as more than about six months, or about one year, among others), while the second biodegradable material may be configured to degrade over a shorter period of time relative to the first biodegradable material, for example three months or less (such as less than about two months, among others).

The composite devices described herein may be made from any combination of at least two different biodegradable materials. In embodiments, the composite device may include a plurality of different biodegradable materials which each degrade at different rates of time upon implantation. Any combination of suitable biodegradable materials may be used in forming the composite devices described herein as long as the two or more biodegradable materials degrade at different rates of time upon implantation and provided the at least one channel is filled with the faster degrading material.

Exemplary biodegradable materials that may be used as the first or second biodegradable materials in forming the composite fixation devices include degradable metals and metal alloys such as magnesium or magnesium alloys, manganese alloys and biodegradable polymeric materials such as poly (lactic acids), poly(glycolic acids), poly(lactic-co-glycolic acids), poly(dioxanones), poly(caprolactones), poly(hydroxyl-alkanoates), poly(trimethylene carbonate), poly(ethylene oxide), poly(hydroxybutyrate), poly(valerolactone), and natural materials such as collagen, cellulose, polysaccharides, polyanhydrides, chitosan, dextran, and copolymers and combinations thereof.

Some non-limiting examples of biodegradable polymeric materials useful as the first biodegradable material include slower degrading polymers made from biodegradable aliphatic polyesters, such as poly(lactic acids), poly(glycolic acids), poly(lactic-co-glycolic acids), poly(dioxanones), poly(caprolactones), poly(hydroxyl-alkanoates), any copolymers based on cyclic aliphatic esters and combinations thereof. Some non-limiting examples of biodegradable polymeric materials useful as the second biodegradable material include faster degrading materials made of aliphatic polyesters, polyphosphazenes, polyanhydrides, calcium carbonate, β-TCP (β-tri-calcium phosphate), hydroxyapatite and combinations thereof.

In embodiments, the first biodegradable material may be a slower degrading polymer described above and the second biodegradable material may be a faster degrading material. In some embodiments, the first and second biodegradable materials may display different degradation times upon implantation, but may be selected from the same group of slower or faster degrading polymers. One non-limiting example includes the use of combinations of degradable polymers such as poly(lactic acid), poly(glycolic acid), poly(caprolactone) and poly(trimethylene carbonate). In such examples, the degradation rates may be controlled by altering the percent of the degradable polymers in each of the first and second biodegradable materials It is further envisioned that the first and second biodegradable materials may be derived from the same material. For example, the first and second biodegradable materials may both be derived from collagen, however the first biodegradable material may be collagen and the second biodegradable material may be derived from oxidized collagen resulting in two materials derived from the same material but degradable at different rates. Where this occurs, at least one of the first and second biodegradable materials may be chemically altered, oxidized, functionalized, cross-linked, polymerized, copolymerized, blended, and the like, to alter the degradation time of the original material.

In embodiments, the composite fixation device may include a body made from a first polymeric material, such as poly(lactic acid), with at least one channel defined therein which contains a second polymeric material such as an aliphatic polyester.

The biodegradable materials useful for forming the composite fixation devices described herein may further include any suitable additives and/or fillers. The additives and/or fillers may include colors, dyes, viscosity-enhancers, emulsifiers, contrast agents (such as Barium and Barium containing polymers), as well as drugs such as antimicrobials, antivirals, chemotherapeutics, antiseptics, analgesics, anti-inflammatory agents, polymeric-drugs, combination thereof, and the like. In some examples, materials may include one or more osteoinductive substances. An osteoinductive substance, as used herein, is any substance that promotes stem cells, immature bone cells, and/or non-bone cell types to mature and/or differentiate into bone cells that facilitate laying down new bone. Exemplary osteoinductive substances that may be included in one or both of the biodegradable materials include bone morphogenetic proteins (such as BMP-1, BMP-2, BMP-3, etc.), Transforming Growth Factor-beta (TGF-β), Epidermal Growth Factor (EGF), Platelet Derived Growth Factor (PDGF), Fibroblast Growth Factors (FGFs), Parathyroid Hormone Related Peptide (PTHrp), Insulin-like Growth Factors (IGFs), combination thereof, and/or the like.

The additional agents and/or fillers may be mixed with the first and/or second materials prior to the formation of the device. In some embodiments, the additional agents may be added to the device after the formation of the device as a coating or through a chemical or physical deposition or impregnating process.

The composite fixation devices of the present teachings may be formed by any suitable method, generally according to the composition and structure of the device. Exemplary methods of forming the two-part device are presented below.

In embodiments, the body of the device may be formed of the first biodegradable material by standard methods of forming fixation devices. For example, a first biodegradable material, with or without a thread or driver-engagement member, may be formed by any suitable process including casting, molding (such as injection-molding, reaction injection molding, extrusion molding, rotational molding, thermoforming, vacuum forming, pressure molding, blow-molding, and the like), machining a nonthreaded shaft, cold- and/or hot-forming, and/or the like.

Alternatively, or in addition, the first biodegradable material may be machined to create the channels defined therein, as well as to form a thread and/or a driver-engagement structure on the device. In embodiments, the channels may be formed in the composite device during the molding or casting process. The channels may be filled with the second biodegradable material either during or after the selected forming process is complete.

The composite fixation devices may be used on any suitable tissue or bone, in any suitable patient (i.e., human, equine, canine, and/or feline species). Exemplary bones to which the fixation device of the present disclosure may be applied include bones of the arms (e.g., radius, ulna, humerus), legs (e.g., femur, tibia, fibula, patella), hands/wrists (e.g., phalanges, metacarpals, and carpals), feet/ankles (e.g., phalanges, metatarsals, and tarsals), vertebrae, scapulas, pelvic bones, cranial bones, ribs, and/or clavicles, among others. Exemplary tissues to which the fixation device of the present disclosure may be applied include, but are not limited too, cartilages, tendons, ligaments, and muscles. In arthroscopic surgery, the devices may be used to attach tissue to bone, bone to bone and/or tissue to tissue.

Composite fixation devices may be used for any suitable purpose in and/or adjacent the bone(s) and/or tissues. In embodiments, the devices may be used to correct a discontinuity in bone and/or tissue. Suitable discontinuities may occur naturally and/or may result from injury, disease, and/or surgical intervention, among others. Accordingly, exemplary discontinuities for use with the composite fixation devices described herein may include joints, fractures (breaks in bones), osteotomies (cuts in bones), and/or nonunions (for example, cartilage tears, ligament strains, snapped tendons, and other gaps produced by injury, disease, and/or a birth defect).

For example, the devices may be configured to span any suitable bone discontinuity (or discontinuities) so that the fasteners fix the relative positions of bone pieces/fragments (and/or bones) disposed on opposing sides of the bone discontinuity (or discontinuities). In some embodiments, the fixation devices may reinforce a bone lacking a discontinuity. Alternatively, or in addition, the fixation device may be used in conjunction with a fixation device, such as a bone plate.

The methods of the present teachings may then be used to fix bones or to fix tissue to bones. Exemplary methods may include any suitable combination of the steps described in the following paragraphs, performed in any suitable order, any suitable number of times.

In embodiments, a method of the present disclosure may include selection of a bone for fixation. Suitable bones and discontinuities are described above. In the case of a fractured bone, the fracture may be reduced before, during, and/or after placement of a composite fixation device of the present disclosure.

One or more composite fixation devices, such as bone screws, may be selected for placement into the bone. The size and number of the fixation devices may be selected, for example, based on the size (such as the diameter) of the bone to be fixed and/or based on the size/severity/disposition of the fracture. One or more non-composite fixation devices may also be used in combination with the devices of the present disclosure. In some examples, a non-composite fixation device, such as a bone plate, may be selected according to the bone to be fixed.

At least one hole may be pre-formed in the bone or tissue. The number of holes formed may correspond to the number of composite fixation devices selected. The hole(s) may extend across a fracture in the bone or may terminate at or before the fracture. The hole(s) may be formed using a hole-forming device, such as a drill. Alternatively, or in addition, the hole(s), or some of the holes among a plurality of holes, or portions of any given hole, may be formed by the fixation devices themselves, particularly self-tapping screws, during their placement into the bone. The hole may be tapped (threaded) or may be nontapped (nonthreaded). The hole may have any suitable size. In some examples, the hole may have a diameter less than the diameter of the composite fixation device selected, or may have a diameter corresponding substantially to the diameter of the fixation device (such as when the hole is also tapped). Furthermore, the hole may have a depth that is less than, about the same as, or greater than, the length of a composite fixation device of the present disclosure.

Each composite fixation device may be placed into a corresponding hole in the bone or tissue. The composite fixation device may be configured to have a head or driver-engagement member to aid in the introduction of the composite fixation device into the bone or tissue. A driver may engage the head or driver-engagement member of each fixation device to either rotate or drive each fixation device into threaded or frictional engagement with the bone or tissue around the hole. The device may be buried in the bone or tissue, may be flush with the bone or tissue, or a proximal and/or distal end of the fastener may protrude above the bone or tissue surface.

Each composite fixation device is designed to be left in the bone or tissue for a suitable length of time to allow the treated bone or tissue to integrate into the device. In some embodiments, the integration of tissue or bone into the device provides further fixation of the device to the surrounding tissue or bone. In some embodiments, one or more of the fixation devices are left in the bone or tissue until the second biodegradable material is degraded, thereby creating openings in the device for the bone or tissue to grow into the device. Alternatively, or in addition, one or more of the biodegradable materials are left in the bone or tissue until the device is substantially degraded by the body.

Turning now to FIG. 1, composite fixation device 110, i.e., a surgical pin, is shown which includes body 120 and channel 130 which is defined within a portion of body 120. Body 120 is made from a first biodegradable material. Channel 130 is defined within a portion of body 120 and extends along an interior portion of body 120. Channel 130 includes a second biodegradable material which degrades faster than the first biodegradable material of body 120. In embodiments, the composite fixation device may include a plurality of channels.

Figure 2:
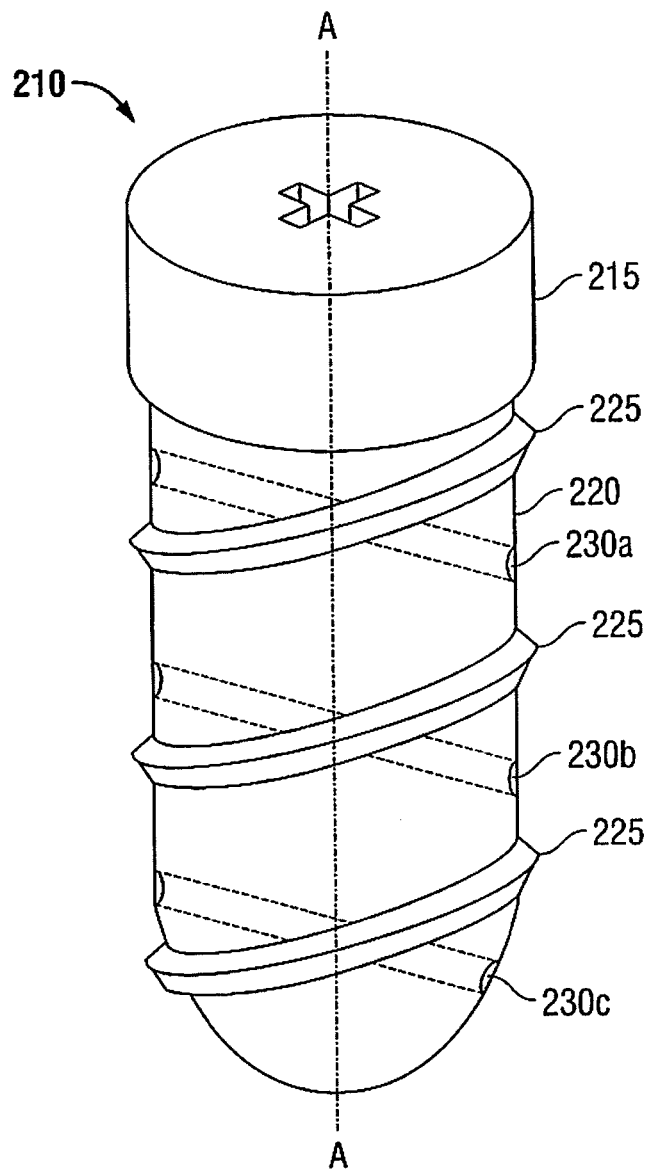
FIG. 2 shows a perspective view of another embodiment of a composite fixation device according to the present disclosure.

Another embodiment of the present disclosure is shown in FIG. 2. The composite fixation device 210 is an interference screw which includes head 215, body 220, and at least one thread 225 which extends axially around the perimeter of body 220. Channels 230*a*, 230*b*, 230*c* pass through the longitudinal axis (A) of body 220 of device 210 and include a second biodegradable material. As shown, channels 230*a-c* are filled with a second biodegradable material to create a surface which is flush with the outer surface of body 220. In the embodiments (not shown), the second biodegradable material may only fill a portion of channels 230*a-c* thereby providing a composite device with a degree of porosity. Alternatively, the second biodegradable material may overfill the channel (not shown) creating bumps on the surface of the device. The addition of bumps to the surface of the device increases the surface area of the device. In some embodiments, each of the channels may include varying levels of the second biodegradable material.

FIG. 3 is a cross-sectional view of a device similar to the device shown in FIG. 2. Channels 330*a*-330*c* are angled between threads 325 and pass through the longitudinal axis (A) of body 320 of device 310. The channels may be angled at any suitable degree relative to the threads. Device 310 also includes head 315 at the proximal end of the device. Head 315 includes driver-engagement member 340 for interacting with a driver (not shown) for implantation.

In embodiments, as shown in FIG. 4, device 410 includes a body 420 and head 415 made from a first biodegradable material and a plurality of interconnected channels 430a-430f wherein at least a portion of channels 430a-430f include a second biodegradable material. Longitudinal channels 430a and 430b are positioned off-center and extend along the longitudinal axis (A) of device 410 while transverse channels 430c-430f pass at least partially through the longitudinal axis (A) and connect longitudinal channels 430a and 430b to each other and/or to the outer surface of the device 410. In embodiments, longitudinal channels 430a-b may be used to engage a driver (not shown).

Figure 5:
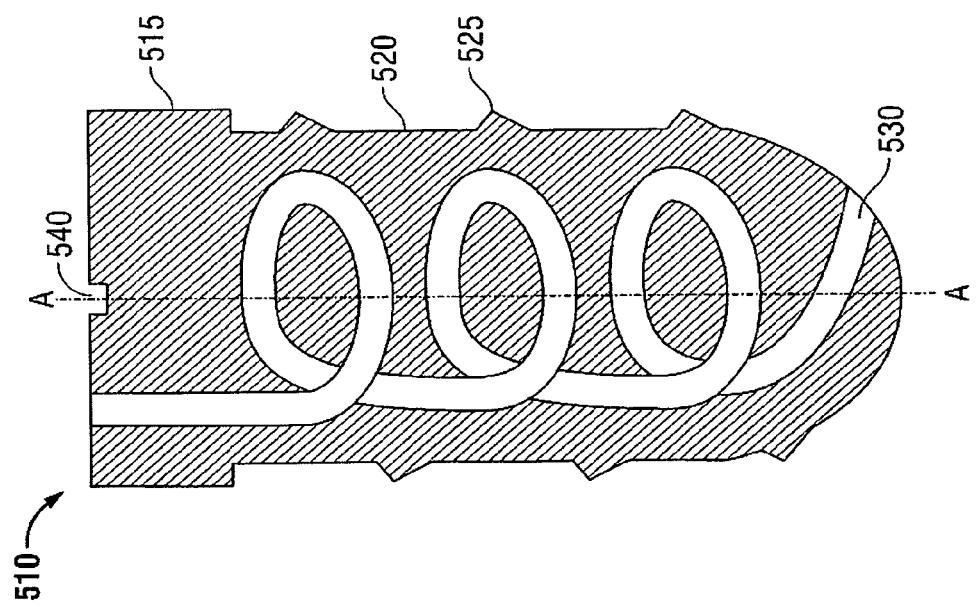
FIG. 5 shows a cross-sectional view of another embodiment of a composite fixation device according to the present disclosure.

In FIG. 5, composite fixation device 510 includes a body 520 and a head 515 made of a first biodegradable material. Head 515 includes driver-engagement member 540. Device 510 also includes channel 530 which forms a helical or coil shape defined within body 520. As shown, the helical shape of channel 530 follows a path opposite that of threads 525. For instance, device 510 may include threads 525 on the exterior of body 520 with a right-hand turn while channel 530 may form a helical shape that theoretically would create a left-hand turn in the interior of body 520. In alternative embodiments, the channel may follow a helical path which parallels the threads on the exterior of the screw.

Figure 6:
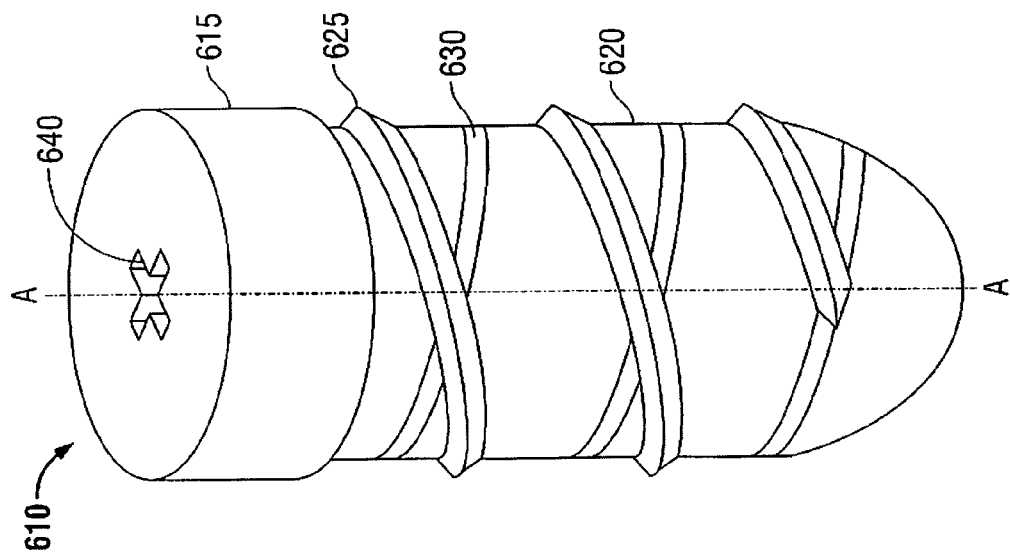
FIG. 6 shows a perspective view of another embodiment of a composite fixation device according to the present disclosure.

As depicted in FIG. 6, in still other embodiments, channel 630 may extend axially along the perimeter of body 620 of device 610, similar to thread 625. However, like FIG. 5, channel 630 follows an axial path opposite threads 625 (i.e., axial path of channel is left-handed turn while axial path of threading is right-handed turn). Channel 630 includes a second biodegradable material which is flush with the outer surface of body 620. It is envisioned that the second biodegradable material of channel 630 will degrade faster than the material used to form thread 625 which creates an opening beneath thread 625 where channel 630 and thread 625 crossover one another. Tissue will grow into the opening behind thread 625 thereby anchoring device 610 into tissue by wrapping around a portion of thread 625. The portions of channel 630 which do not pass under thread 625 will also degrade faster than first biodegradable material of body 620 thereby creating indentations for tissue to grow into, thereby creating threads in the tissue to further anchor the device in place. Device 610 also includes head 615 having driver-engagement member 640 centrally positioned along the longitudinal axis (A).

Figure 7:
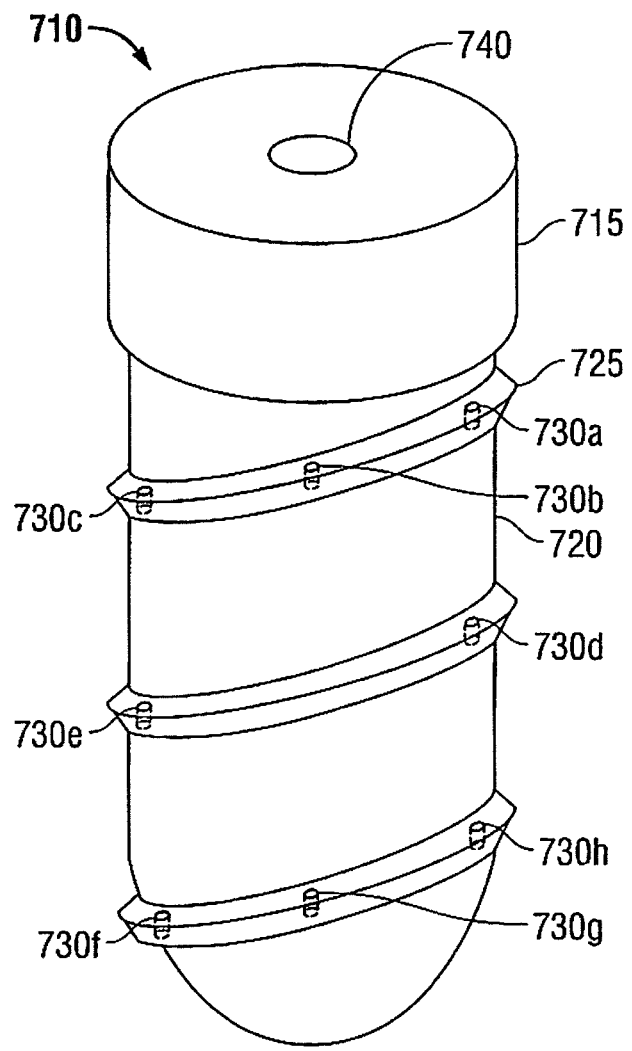
FIG. 7 shows a perspective view of another embodiment of a composite fixation device according to the present disclosure.

As shown in FIG. 7, device 710 includes a body 720 made of a first biodegradable material. Device 710 also includes head 715 with driver engagement member 740 and thread 725 extending axially about the perimeter of body 720. Thread 725 includes a plurality of channels 730a-h which contains a second biodegradable material. Upon implantation, the second biodegradable material of channels 730a-h will degrade faster than the material which forms thread 725, thereby creating a plurality of openings in thread 725 for tissue to grow into. Tissue will grow into the openings and pass through a portion of thread 725 thereby anchoring device 710 into tissue.

It will be understood that various modifications may be made to the embodiments disclosed herein. Therefore, the above description should not be construed as limiting, but merely as an exemplification of useful embodiments. Those skilled in the art will envision other modifications within the scope and spirit of this disclosure. Various modifications and variations of the composite fixation devices and uses thereof will be apparent to those skilled in the art from the foregoing detailed description. Such modifications and variations are intended to come within the scope of the following claims.

What is claimed is:

1. A composite fixation device comprising:
   a body defining a longitudinal axis and made from a first biodegradable material, the body including a thread extending axially around an outer perimeter of the body; and
   at least one channel defined within the body, passing from a first portion of the outer perimeter of the body through the longitudinal axis to a second portion of the outer perimeter of the body and angled between the thread, at least a portion of the channel filled with a second biodegradable material.

2. The composite fixation device of claim 1, wherein the first biodegradable material is selected from the group consisting of poly(lactic acids), poly(glycolic acids), poly(lactic-co-glycolic acids), poly(dioxanones), poly(caprolactones), poly(hydroxyl-alkanoates), copolymers based on cyclic aliphatic esters, and combinations thereof.

3. The composite fixation device of claim 1, wherein the first biodegradable material comprises poly(lactic acid).

4. The composite fixation device of claim 1, wherein the second biodegradable material is selected from the group consisting of aliphatic polyesters, polyphosphazenes, polyanhydrides, calcium carbonate, β-tri-calcium phosphate, hydroxyapatite, and combinations thereof 5. The composite fixation device of claim 1, wherein the second biodegradable material comprises an aliphatic polyester.

6. The composite fixation device of claim 1, wherein the device is a surgical pin.

7. The composite fixation device of claim 1, wherein the first biodegradable material degrades in greater than 3 months following implantation.

8. The composite fixation device of claim 7, wherein the second biodegradable material degrades in less than 3 months following implantation.

9. The composite fixation device of claim 1, wherein the device is an interference screw.

10. The composite fixation device of claim 1, wherein the first biodegradable material comprises collagen and the second biodegradable material comprises oxidized collagen.

11. The composite fixation device of claim 1, wherein the first biodegradable material is selected from the group consisting of poly(lactic acids), poly(glycolic acids), poly(lactic-co-glycolic acids), poly(dioxanones), poly(caprolactones), poly(hydroxyl-alkanoates), copolymers based on cyclic aliphatic esters, and combinations thereof, and the second biodegradable material is selected from the group consisting of polyphosphazenes, polyanhydrides, calcium carbonate, β-tri-calcium phosphate, hydroxyapatite, and combinations thereof.

12. The composite fixation device of claim 1, wherein the first biodegradable material degrades in greater than about 6 months following implantation and the second biodegradable material degrades in less than about 2 months following implantation.

13. The composite fixation device of claim 1, further comprising a plurality of the channels.

14. The composite fixation device of claim 1, wherein the channel is filled with the second biodegradable material.

* * * * *